US012800594B2

(12) United States Patent
Dobromyslin et al.

(10) Patent No.: US 12,800,594 B2
(45) Date of Patent: Nov. 17, 2026

(54) MICROFLUIDIC IMAGE ANALYSIS SYSTEM

(71) Applicant: Instrumentation Laboratory Co., Bedford, MA (US)

(72) Inventors: Vitaly Dobromyslin, Bedford, MA (US); Shankar Balasubramanian, Bedford, MA (US)

(73) Assignee: Instrumentation Laboratory Co., Bedford, MA (US)

( * ) Notice: Subject to any disclaimer, the term of this patent is extended or adjusted under 35 U.S.C. 154(b) by 0 days.

(21) Appl. No.: 19/178,064

(22) Filed: Apr. 14, 2025

(65) Prior Publication Data

US 2025/0389735 A1 Dec. 25, 2025

Related U.S. Application Data

(63) Continuation of application No. 18/443,138, filed on Feb. 15, 2024, now Pat. No. 12,345,719, which is a (Continued)

(51) Int. Cl.

*G01N 33/72* (2006.01)
*B01L 3/00* (2006.01)
*G06T 7/00* (2017.01)

(52) U.S. Cl.

CPC ...... *G01N 33/726* (2013.01); *B01L 3/502715* (2013.01); *G06T 7/0012* (2013.01); (Continued)

(58) Field of Classification Search

CPC . G06T 2207/30072; G06T 2207/30168; G06T 7/97; G06T 7/0012; G06N 3/08; G06N 20/00; G06V 10/764

See application file for complete search history.

(56) References Cited

U.S. PATENT DOCUMENTS 4,724,330 A 2/1988 Tuhro
6,049,381 A 4/2000 Reintjes et al.
(Continued)

FOREIGN PATENT DOCUMENTS

CN 102982314 B 5/2016
CN 111754481 A 10/2020
(Continued)

OTHER PUBLICATIONS

Ang Guo, "Delineating regions of interest for mass spectrometry imaging by multimodally corroborated spatial segmentation", Mar. 13, 2023 (Year: 2023).*
(Continued)

*Primary Examiner* — Maurice C Smith
(74) *Attorney, Agent, or Firm* — ARENTFOX SCHIFF LLP

(57) ABSTRACT

Technology described herein includes a method that includes obtaining an image of a fluid of a microfluidic analysis system. The microfluidic analysis system includes or receives a container that contains the fluid for measurement of analyte or quality determination. A region of interest (ROI) is identified based on the image. The ROI is a set of pixel values for use in the measurement of the analyte or the quality determination of the fluid, fluidic path, or measuring system. Identifying the ROI includes: determining an alignment of the container of the fluid with the imaging device based on the image, and identifying the ROI based on information about the measurement of the fluid or based on information about non-analyte features of the fluid. An analysis of the image of the fluid is performed using the set of pixel values of the ROI.

20 Claims, 8 Drawing Sheets

Related U.S. Application Data continuation of application No. 17/555,939, filed on Dec. 20, 2021, now Pat. No. 11,940,451.

(52) U.S. Cl.
CPC ......... *G06T 7/97* (2017.01); *B01L 2300/0663* (2013.01); *G06T 2207/30072* (2013.01); *G06T 2207/30168* (2013.01)

(56) References Cited

U.S. PATENT DOCUMENTS

| | | | | |
|---|---|---|---|---|
| 8,538,122 | B2 | 9/2013 | Schlarb et al. | |
| 9,324,145 | B1 | 4/2016 | Cherevatsky et al. | |
| 9,506,935 | B2 | 11/2016 | Huet et al. | |
| 9,824,441 | B2 | 11/2017 | Satish et al. | |
| 11,940,451 | B2 | 3/2024 | Dobromyslin et al. | |
| 2006/0050966 | A1* | 3/2006 | Nishimura | G06T 7/136 382/209 |
| 2012/0093399 | A1* | 4/2012 | Paik | H04N 23/743 382/164 |
| 2018/0052147 | A1 | 2/2018 | Zeng et al. | |
| 2018/0053297 | A1 | 2/2018 | Celenk et al. | |
| 2020/0057880 | A1 | 2/2020 | Mizutani et al. | |
| 2020/0103395 | A1 | 4/2020 | Bosy et al. | |
| 2020/0294231 | A1 | 9/2020 | Tosun et al. | |
| 2020/0327377 | A1 | 10/2020 | Jaganathan et al. | |
| 2021/0270722 | A1 | 9/2021 | Chou et al. | |
| 2021/0283607 | A1 | 9/2021 | Augustsson et al. | |
| 2021/0293803 | A1 | 9/2021 | Azhar et al. | |
| 2023/0194555 | A1 | 6/2023 | Dobromyslin et al. | |

FOREIGN PATENT DOCUMENTS

| | | | |
|---|---|---|---|
| CN | 112689763 | A | 4/2021 |
| WO | 2018/065626 | A1 | 4/2018 |
| WO | 2020/025684 | A1 | 2/2020 |
| WO | 2020/027923 | A1 | 2/2020 |

OTHER PUBLICATIONS

Kyriacos Yiannacou, "Controlled Manipulation and Active Sorting of Particles Inside Microfluidic Chips Using Bulk Acoustic Waves and Machine Learning" Apr. 2, 2021 (Year: 2021).*
U.S. Provisional Application filled on Oct. 2, 2018, by Bosy et al., 62/740,117.
Canny, John, "A computational approach to edge detection", IEEE Transactions on Pattern Analysis and Machine Intelligence, vol. 6, No. 6, Nov. 1986, pp. 679-698.
Extended European Search Report in European Appln. No. 22186421.8, dated Mar. 3, 2023, 7 pages.
Otsu, Nobuyuki, "A threshold selection method from gray-level histograms", IEEE Transactions on Systems, Man, and Cybernetics, vol. 9, No. 1, Jan. 1979, pp. 62-66.
U.S. Provisional Application filled Oct. 2, 2018, by Bosy et al., U.S. Appl. No. 62/740,117.
Walt et al., "scikit-image: image processing in Python", PeerJ, e453, vol. 2, Jun. 2014, pp. 1-18.
Yiannacou et al., "Controlled Manipulation and Active Sorting of Particles Inside Microfluidic Chips Using Bulk Acoustic Waves and Machine Learning", Langmuir, vol. 37, Apr. 2, 2021, pp. 4192-4199.
Office Action received for European Patent Application No. 22186421.8, mailed on May 22, 2025, 5 pages.

* cited by examiner

MICROFLUIDIC IMAGE ANALYSIS SYSTEM

CROSS REFERENCE TO RELATED APPLICATION

This patent application is a continuation (and claims the benefit of priority under 35 USC 120) of U.S. patent application Ser. No. 18/443,138, filed Feb. 15, 2024, which is a continuation (and claims the benefit of priority under 35 USC 120) of U.S. patent application Ser. No. 17/555,939, filed Dec. 20, 2021. The disclosure of the prior applications is considered part of (and is incorporated by reference in) the disclosure of this application.

TECHNICAL FIELD

This specification generally relates to microfluidic image analysis devices.

BACKGROUND

A microfluidic analysis device performs analysis of the physical and chemical properties of fluids at a microscale. A microfluidic image analysis device often includes a camera that captures an image of the sample fluid. The captured image may be processed to determine various physical and chemical properties of the fluid.

SUMMARY

In one aspect, this document describes a method for microfluidic analysis of fluids. The method includes obtaining an image of a fluid of a microfluidic analysis system, wherein the microfluidic analysis system includes or receives a container that contains the fluid for measurement of analyte or quality determination, and the image is captured using an imaging device associated with the microfluidic analysis system; identifying, based on the image, a region of interest (ROI), wherein the ROI is a set of pixel values for use in the measurement of the analyte or the quality determination of the fluid, fluidic path, or measuring system and wherein identifying the ROI includes: determining an alignment of the container of the fluid with the imaging device based on the image, and identifying the ROI based on information about the measurement of the fluid or based on information about non-analyte features of the fluid; and performing an analysis of the image of the fluid using the set of pixel values of the ROI.

In another aspect, this document describes a system for microfluidic analysis of fluids. The system includes a microfluidic analysis apparatus that includes or receives a container configured to hold a fluid for measurement of analyte or quality determination; an imaging device configured to obtain an image of the fluid in the container; and one or more processing devices configured to perform various operations. The operations include identifying, based on the image, a region of interest (ROI), wherein the ROI is a set of pixel values for use in the measurement of the analyte or the quality determination of the fluid, fluidic path, or the microfluidic analysis apparatus, and wherein identifying the ROI includes: determining an alignment of the container of the fluid with the imaging device based on the image, and identifying the ROI based on information about the measurement of the fluid or based on information about non-analyte features of the fluid; and performing an analysis of the image of the fluid using the set of pixel values of the ROI.

In another aspect, this document describes a non-transitory, computer-readable medium storing one or more instructions executable by a computer system to perform various operations. The operations include obtaining an image of a fluid of a microfluidic analysis system, wherein the microfluidic analysis system includes or receives a container that contains the fluid for measurement of analyte or quality determination, and the image is captured using an imaging device associated with the microfluidic analysis system; identifying, based on the image, a region of interest (ROI), wherein the ROI is a set of pixel values for use in the measurement of analyte or the quality determination of the fluid, fluidic path, or measuring system and wherein identifying the ROI includes: determining an alignment of the container of the fluid with the imaging device based on the image, and identifying the ROI based on information about the measurement of the fluid or based on information about non-analyte features of the fluid; and performing an analysis of the image of the fluid using the set of pixel values of the ROI.

Implementations of the above aspects can include one or more of the following features. The fluid is a whole blood sample, and the image represents the whole blood sample with blood plasma separated from red blood cells. Identifying the ROI includes identifying, in the image, a portion representing the blood plasma, wherein identifying the portion representing the blood plasma includes: detecting a plurality of reference features associated with the container of the fluid; identifying, based on the reference features, a candidate region for the ROI; and performing clustering-based thresholding of pixel values within the candidate region to identify the portion representing the blood plasma. Alternative implementations may use neural networks for ROI detection and image segmentation instead of the clustering-based thresholding. The measurement of the analyte includes a parameter indicative of hemolysis (hemoglobin) in a portion representing blood plasma. The measurement of the analyte includes a parameter indicative of lipemia (or lipids) in a portion representing blood plasma. The measurement of the analyte includes a parameter indicative of Icterus (or bilirubin) in a portion representing blood plasma. The method or the operations can further include determining that the ROI excludes a portion that represents lipid in blood plasma; and identifying an updated ROI such that the updated ROI includes a bounding box that includes the portion that represents the lipid. The quality determination of the fluid, the fluidic path, or the measuring system includes: determining quality of an assay, determining quality of a sample, and determining integrity of the fluidic path or the measuring system impacting the ROI. The quality determination of the fluid, the fluidic path, or the measuring system includes: determining that the ROI includes a portion that represents an air bubble in the fluid; and identifying an updated ROI such that the updated ROI excludes the portion that represents the air bubble. The method or the operations can further include detecting an amount of tilt in the image of the fluid, the tilt resulting from the alignment of the container of the fluid with the imaging device; and generating, based on the amount of the tilt, a rotation-corrected image of the fluid, wherein the ROI is identified in the rotation-corrected image. Performing the analysis of the image of the fluid includes: generating an image focus score associated with the image; determining that the image focus score is lower than a predetermined threshold; and discarding the image of the fluid responsive to determining that the image focus score is lower than the predetermined threshold. Performing the analysis of the image of the fluid includes:

identifying, in the image, a portion representing a transparent portion of the container; and using brightness of the portion representing the transparent portion of the container as a reference point to evaluate brightness of other portions of the image. The method or the operations can further include monitoring one or more optical characteristics of the fluid at predetermined intervals. The method or the operations can further include identifying a target optical interference pattern in the image; and generating an alert in response to identifying the target optical interference pattern in the image. The blood plasma is separated from the red blood cells within the microfluidic analysis apparatus using 2-150 uL of the whole blood sample.

Particular implementations of the subject matter described in this disclosure can be implemented to realize one or more of the following advantages. The implementations of the present disclosure can perform microfluidic analysis by implementing machine vision processes that are adaptive and automatic. The described microfluidic analysis system can identify a region of interest (ROI) in images of fluids even when the characteristics of the ROI vary significantly, e.g., when the ROI does not have fixed shape, fixed image intensity, or fixed location in the corresponding containers of the fluids, and so on. As such, the disclosed technology can account for any alignment-variation between an imaging system and the unit/entity (e.g., a container) that the imaging system captures. The disclosed technology can also account for inhomogeneity of a sample (e.g., whole blood) by automatically including or excluding elements such as air bubbles, lipids etc., to identify an accurate ROI suited for a specific application. In certain microfluidic analysis systems—e.g., in whole blood analysis systems, where accurate identification of the region of interest governs the accuracy of the results—the adaptive and automatic ROI identification can improve the underlying technology in various ways. For example, implementations of the present disclosure can automatically identify ROIs while improving processing time as well as accuracy attributable to potential human errors.

In some implementations, by monitoring one or more optical characteristics of a fluid at predetermined intervals or at every instance, the automated and adaptive processes described herein can facilitate a substantially continuous quality control of various aspects (e.g., the quality of an assay, the quality of a sample, or the integrity of the fluidic path or the measuring system impacting the ROI) of the underlying system. For example, the microfluidic analysis system can identify a target optical interference pattern in the image, e.g., one that is representative of an air bubble or poor ROI region in an image of a blood sample, and can send an alert to a user of the imaging device accordingly, and/or discard samples that do not meet target quality criteria.

It is appreciated that methods and systems in accordance with the present disclosure can include any combination of the aspects and features described herein. That is, methods and systems in accordance with the present disclosure are not limited to the combinations of aspects and features specifically described herein, but also may include any combination of the aspects and features provided.

The details of one or more implementations of the present disclosure are set forth in the accompanying drawings and the description below. Other features and advantages of the present disclosure will be apparent from the description and drawings, and from the claims.

BRIEF DESCRIPTION OF DRAWINGS

Like reference numbers and designations in the various drawings indicate like elements.

DETAILED DESCRIPTION

In various fluidic and microfluidic applications, accurate identification of a region of interest (ROI) can be very important. For example, hemolysis detection/measurement entails separating whole blood into red blood cells and plasma, and then measuring an amount of hemoglobin in the plasma. Therefore, for accurate image-based hemolysis detection and measurement, it is important to accurately identify an ROI in the image such that the ROI includes only the plasma region and excludes the red blood cells as well as other artifacts such as air bubbles. A microfluidic image analysis device can include, or can receive, a container (e.g., a cartridge, a vial, a cuvette, or others) that contains a sample fluid (e.g., whole blood sample that is then separated into red blood cells and plasma) for analysis. An image capture device such as a camera can be used to capture an image of the sample fluid such that the captured image can be processed by machine vision processes to determine one or more physical and chemical properties of the fluid. Typical microfluidic analysis systems often identify an ROI based on predetermined assumptions about the ROI such as a predetermined shape and/or a predetermined location within the container of the fluid. In practice though, such assumptions can lead to potential inaccuracies. For example, the relative location/orientation of a container with respect to the image capture device can vary from one instance (e.g., measurement or test) to another, rendering any assumptions based on a fixed size or location of the ROI susceptible to inaccuracies. Also, in some cases, there may be impurities (e.g., air bubbles) present within the ROI that need to be accounted for. The technology described in this document provides for adaptive, automatic systems and processes that identify ROIs in images without predetermined assumptions with respect to the shape, location, and/or orientation of the ROIs. Specifically, in some implementations, the disclosed technology uses particular features of the container (e.g., edges) as reference features to correct for any orientation/location variations and facilitates determination of sample-specific, arbitrary-shaped ROIs while potentially accounting for impurities, particles within the ROIs.

Figure 1:
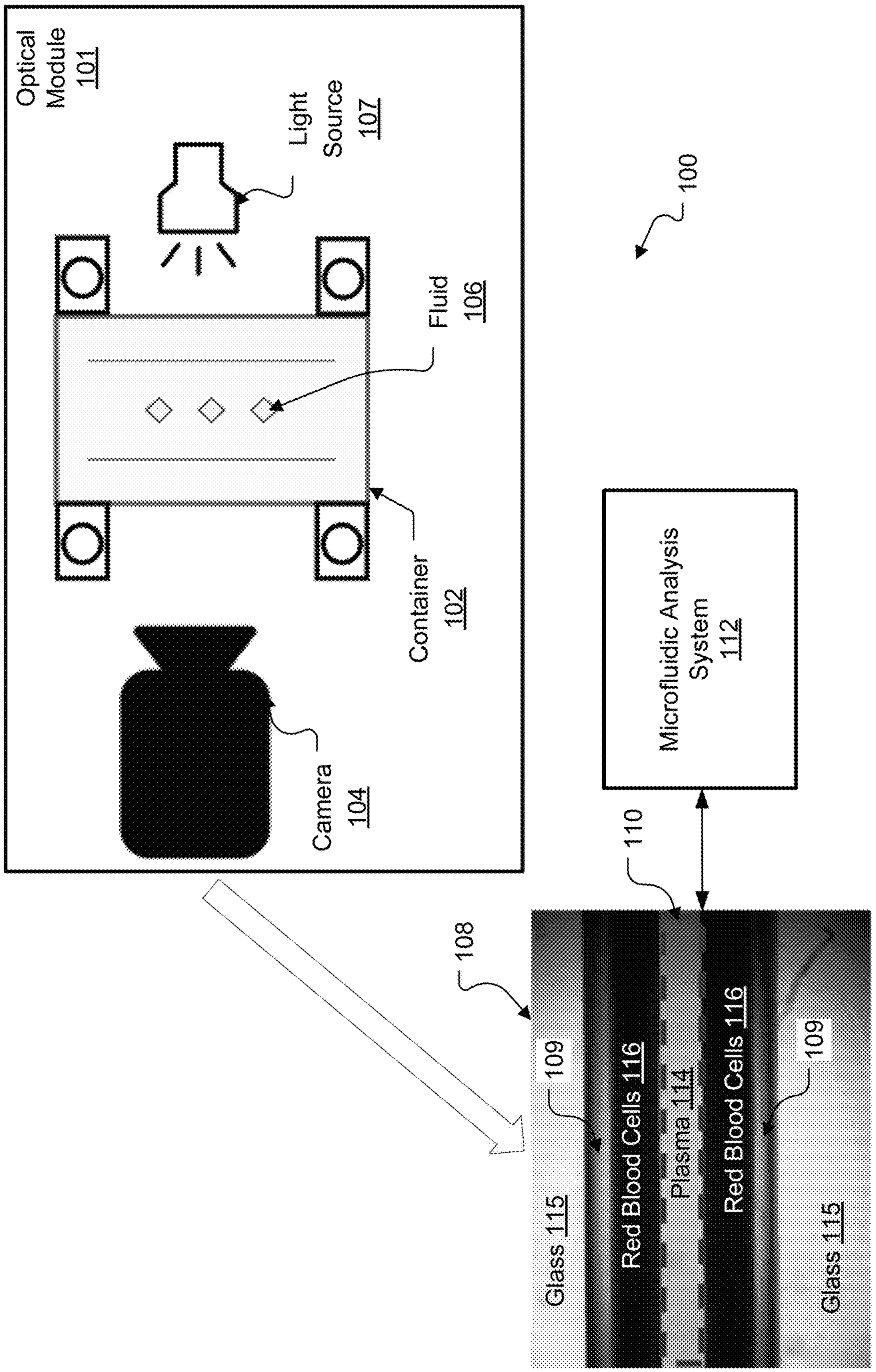
FIG. 1 is a diagram of an example device configured to implement technology described herein.

FIG. 1 is a diagram of an example sample analysis device 100 configured to implement technology described herein. The sample analysis device 100 includes an optical module 101 and a microfluidic analysis system 112 in communication with the optical module 101. The optical module 101 is configured to obtain an image of a fluid 106 in a container 102. In some implementations, the fluid 106 can be configured to flow through the container 102 or can be contained within the container 102. In some implementations, the container 102 is a cartridge within which a whole blood sample may be separated into red blood cells and plasma for hemolysis detection/measurement.

In some implementations, the container 102 is included as a part of the optical module 101. For example, the container 102 can be a microchannel fluid container that is a built-in component or an inserted or add-on component of the optical module 101. In some implementations, the optical module 101 is configured to receive the container 102, e.g., as a disposable cartridge. In some implementations, the container 102 can be a microfluidic flow-cell.

In some implementations, the sample analysis device 100 can include an acoustic transducer. The acoustic transducer can be, for example, a piezo-electric transducer that is arranged in close proximity to the container 102 such that acoustic energy can be applied by the acoustic transducer to the fluid 106 in the container 102. For example, the acoustic transducer can be activated by an electrical signal to generate acoustic energy that causes separation of red blood cells from plasma in a whole blood sample. In some implementations, the container 102 is a flow cell, and the piezo-electric transducer is bonded to or part of the flow-cell. In such cases, the acoustic energy transmitted to the fluid within the flow-cell can vary depending on the properties of the bond (e.g. bond strength, thickness, etc.).

The optical module 101 can also include a light source 107. The light source 107 is arranged to transmit light waves through the container 102 to the fluid 106 that is flowing through or contained (e.g., stationary without flowing) in the container 102. For example, the light source 107 can be configured to transmit the light waves through a plasma portion of the blood sample that is separated from red blood cells in a whole blood sample. In some implementations, the light source 107 can include a multi-color light emitting diode, e.g., a 2-color LED emitting red and yellow lights. The optical module 101 can include a camera 104, or another optical sensor configured to generate an image 108 of the fluid 106. In some implementations, the camera 104 can include an imaging lens and an aperture. The image 108 can be a grayscale image or a color image, which is then analyzed by the microfluidic analysis system 112.

The specific example of the image 108 shown in FIG. 1 pertains to hemolysis detection/measurement where a blood sample is separated into plasma and red blood cells. In some implementations, plasma separation from the red blood cells can be performed by centrifuging the whole blood sample. Plasma separation from the red blood cells using acoustic applications is also described in U.S. Ser. No. 15/791,734, the entire content of which is incorporated herein by reference. The scope of the disclosed technology however is not limited to hemolysis detection/measurement only, and can be extended to other applications (e.g., colorimetric measurements of analytes in blood). The specific arrangements of the device components as described above and shown in FIG. 1 do not affect implementations of the methods and systems described in this disclosure. As described below, the technology uses information from an image of a sample fluid and selected information of the device arrangement to automatically determine the ROI that is specific to the image.

In the particular example of hemolysis detection shown in FIG. 1, the image 108 includes portions that correspond to the container 102—including transparent areas 115, e.g., glass or other transparent materials, and flow-cell edges 109—and portions that correspond to the whole blood sample, which are located between the flow-cell edges 109. The image 108 shows that the plasma 114 has been separated from the red blood cells 116. This separation allows clear plasma to be interrogated optically to determine a hemoglobin level in the plasma 114. As such, in this particular example of hemolysis detection, the region 110 corresponding to the plasma 114 (shown using the dashed box) is the ROI.

The characteristics of an ROI, e.g., the plasma ROI 110, can vary significantly from one instance to another for various reasons. For example, in implementations, where the container 102 is a flow-cell and the piezo-electric transducer is bonded to the flow-cell, imperfections in the bonding process can introduce bond variations from one flow-cell to another, causing the ROI 110 to potentially assume varying shapes and positions during the process of separating the red blood cells 116 from plasma 114. Another source of variation affecting the ROI 110 can be some unintentional relative tilt between the container 102 and the camera 104 introduced during inserting/assembling the container 102 (e.g., the flow-cell). In some implementations, ROI image intensity variation can also arise due to subtle differences in illumination and camera sensitivity.

In some implementations, sample-to-sample variation can also cause variations in the ROI. For example, concentration of particles in the fluid 106 can determine how much acoustic energy is needed to create the particle-free ROI 110 within the field of view of the camera. Insufficient acoustic energy delivered to the sample containing high particle concentration can lead to an area that is too small for subsequent analytical optical absorbance measurement to be performed. Another major sample-dependent source of image variation (and by extension, a variation in the ROI) is the concentration of light scattering particles such as lipids. The presence of such light scattering particles can make the images appear darker than that expected in accordance with the light absorbing properties of the particles of interest. In some implementations, presence of air or other gas bubbles within ROIs can be sources of variations in the ROI.

The microfluidic analysis system 112 can be configured to account for the different variations in the ROI and identify sample-specific ROIs. The microfluidic analysis system 112 can be implemented using one or more processing devices.

The one or more processing devices can be located at the same location as the optical module 101, or reside on one or more servers located at a remote location with respect to the optical module 101. The microfluidic analysis system 112 can be configured to identify the ROI 110 in the image 108 captured by the optical module 101. The identified ROI is a set of pixel values that are then used in the measurement of an analyte or in determining the quality of the fluid, fluidic path, or other portions of the sample analysis device 100.

The microfluidic analysis system 112 can be configured to perform an analysis of the image 108 of the fluid 106 using a set of pixel values of the ROI. The analysis can include, for example, measurement of one or more analytes in the fluid, or determination of the quality of the fluid, fluidic path, or measuring system. For example, the system 112 can be configured to perform measurements (e.g., hemolysis detection measurement) on blood plasma separated from the blood cells in a whole blood sample. In some implementations, the system 112 can be configured to evaluate sample quality, for example, by determining/detecting the presence of a clot in the sample, and/or identifying non-analyte features that can potentially interfere with accuracy of measurements, e.g., a tilted image, an out-of-focus image, and so on.

Figure 2:
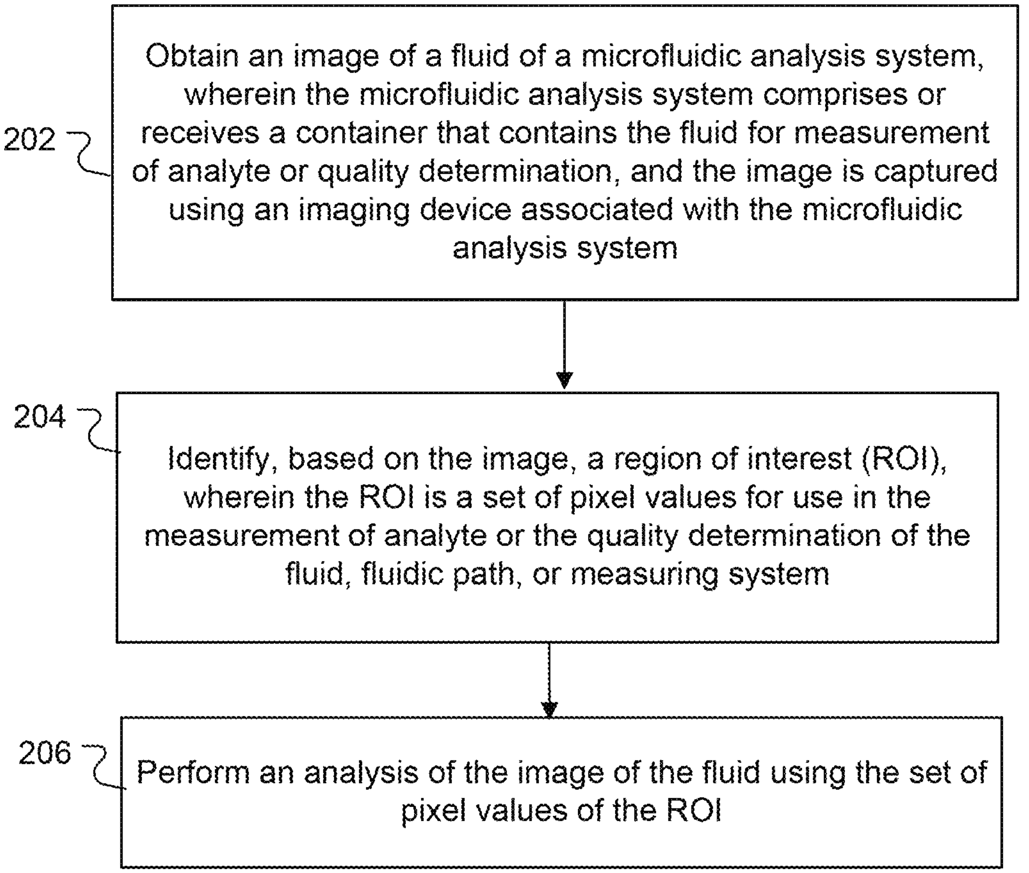
FIG. 2 is a flowchart of an example process for performing microfluidic analysis in accordance with technology described herein.

FIG. 2 is a flowchart of an example process 200 performing microfluidic analysis in accordance with technology described herein. In some implementations, at least a portion of the process 200 may be executed by one or more processing devices associated with the microfluidic analysis system 112 described with reference to FIG. 1. In some implementations, at least a portion of the process 200 may be executed by the optical module 101. In some implementations, at least a portion of the process 200 may be executed at one or more servers (such as servers or computing devices in a distributed computing system), and/or one or more mobile devices (such as smartphones) in communication with the sample analysis device 100 described with reference to FIG. 1.

Operations of the process 200 include obtaining an image of a fluid of a microfluidic analysis system (202). The microfluidic analysis system includes or receives a container that contains the fluid for measurement of analyte or quality determination. The image is captured using an imaging device associated with the microfluidic analysis system. In some implementations, the container can be substantially similar to the container 102 described above with reference to FIG. 1. For example, as shown in FIG. 1, the fluid within the container can be a whole blood sample, and the image can represent the whole blood sample with blood plasma separated from red blood cells. The blood plasma can be separated from the red blood cells locally on the sample analysis device 100 depicted in FIG. 1. In some implementations, the sample size of the whole blood can be in the range 2-150 uL.

Operations of the process 200 also include identifying, based on the image, an ROI (204). The ROI is a set of pixel values for use in the measurement of an analyte or the quality determination of the fluid, fluidic path, or measuring system. Because the ROI may not have fixed shape, fixed image intensity, or fixed location, correctly identifying the ROI can potentially affect the accuracy of the measurement of the analyte in the ROI or performing quality determination of the fluid, fluidic path, or the measuring system.

In some implementations, identifying the ROI can include determining an alignment of the container of the fluid with the imaging device based on the image. For example, an alignment can be determined by first calculating a flow-cell tilt and then finding the location of the flow-cell edges. For example, an alignment/orientation of the container with respect to the image capture device (e.g., the camera 104 in FIG. 1) can be dynamically measured (e.g., each time a new container is inserted or received within the optical module 101), and any misalignment/tilt can be accounted for prior to identifying the ROI (such as correcting for any misalignment during device shipment or from vibration during device use)

In some implementations, identifying the ROI can include identifying the ROI based on information about the measurement of the fluid. For example, an ROI of a high lipid sample can be in the shape of a bounding box. As another example, for reference fluid, an ROI can be in a rectangular shape with specified dimensions relative to the inner flow-cell wall. As another example, an ROI for a blood sample can be dynamically calculated.

In some implementations, identifying the ROI can be based on information about non-analyte features represented in the image. For example, the ROI can be identified based on edges of a container or other fiducial markers represented in the image.

Figure 3B:
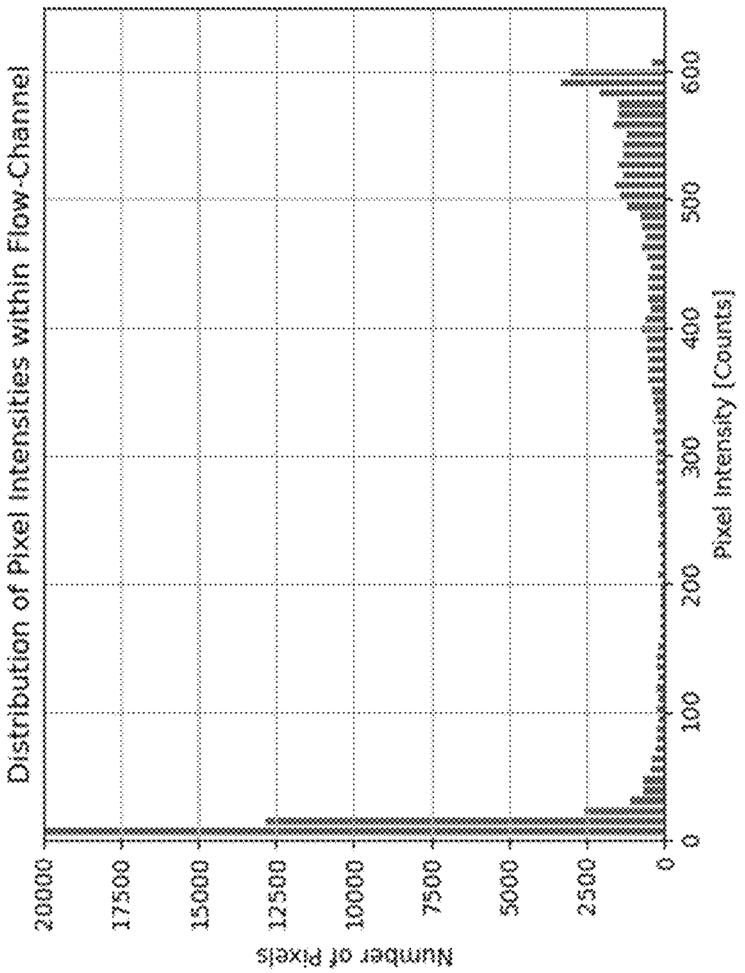
FIG. 3B shows an example of clustering-based thresholding.
Figure 3A:
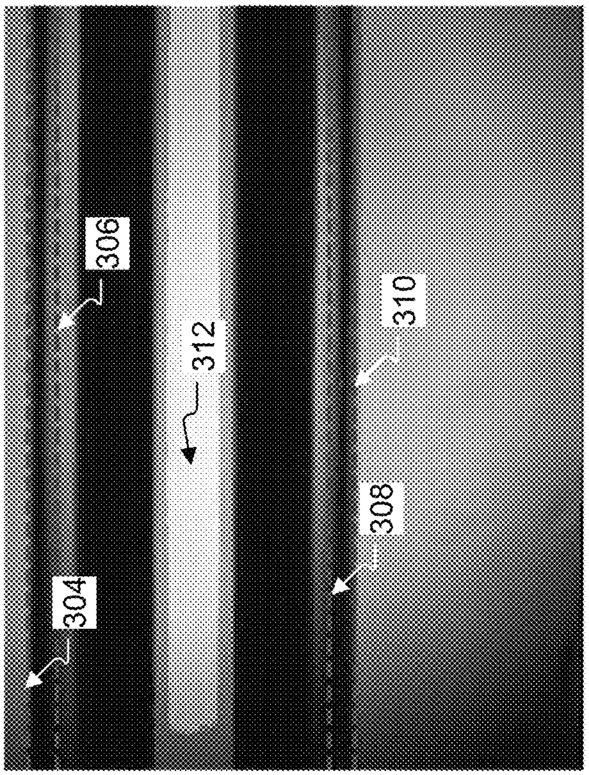
FIG. 3A shows an example of an ROI identified in an image of a whole blood sample.

Referring to FIG. 1, in some implementations, identifying the ROI 110 can include identifying, in the image 108, a portion 110 representing the blood plasma 114. In some implementations, identifying the portion representing the blood plasma can include: detecting a plurality of reference points associated with the container of the fluid, identifying, based on the reference points, a candidate region for the ROI, and performing clustering-based thresholding of pixel values within the candidate region to identify the portion representing the blood plasma. This is illustrated with an example in FIG. 3A. Specifically, FIG. 3A shows an example of an ROI identified in an image of a whole blood sample. In this example, a plurality of reference features associated with the container of the fluid—e.g., the edges 304, 306, 308, and 310 of the flow-cell—are first identified. Various edge detection algorithms-such as the Canny Edge Detection algorithm (Canny, John. "A computational approach to edge detection." IEEE Transactions on pattern analysis and machine intelligence 6 (1986): 679-698.)—can be used for this purpose. Next, the system can be configured to determine which edges correspond to the top inner edge 306 of the flow-cell and the bottom inner edge 308 of the flow-cell. For example, the system can iterate through the candidate edges starting from top to bottom, and sequentially find the top outer edge 304, the top inner edge 306, the bottom inner edge 308, and the bottom outer edge 310.

Once the reference features are identified, the system can be configured to identify, based on the reference features, a candidate region for the ROI. For example, after detecting the inner edges 306 and 308 of the flow-cell, the system can identify a candidate region for the ROI as a region between the top inner edge 306 and the bottom inner edge 308. In the example of FIG. 3A, the candidate region can include both the plasma region and the red blood cells region.

In some implementations, identifying the actual ROI (e.g., the blood plasma region 312 in FIG. 3A) within the candidate ROI can include performing clustering-based thresholding of pixel values within the candidate region. An example of such clustering is shown in FIG. 3B, where multiple clusters of pixel intensities are generated, and one or more threshold values are then used to determine the actual ROI. Various clustering algorithms and tools may be used for this purpose. FIG. 3B shows an example of clustering-based thresholding described in the following publication-Otsu, Nobuyuki. "A threshold selection method from gray-level histograms." IEEE transactions on systems, man, and cybernetics 9.1 (1979): 62-66—the entire content of which is incorporated herein by reference. Specifically, FIG. 3B shows an example of the distribution of the pixel intensities within the candidate region, i.e., the region of the image in FIG. 3A between the top inner edge 306 and the bottom inner edge 308. In this example, an assumption is made that the candidate region for the ROI has two classes of pixels, i.e., red blood cells and plasma, and due to differential light absorbing properties of red blood cells and plasma, the plasma pixels are brighter than the red blood cell pixels. Under these assumptions, multiple clusters of pixels may be identified in the histogram according to their pixel intensities, and an appropriate threshold may be used to separate the plasma pixels from the red blood cells pixels. While the example of FIG. 3B shows two peaks or clusters, in other applications, multiple clusters may be present, and as such, multiple ROIs may be identified. In some implementations, alternatively, one or more neural networks can be used for ROI detection and image segmentation instead of or in addition to the clustering-based thresholding described herein.

Figure 3C:
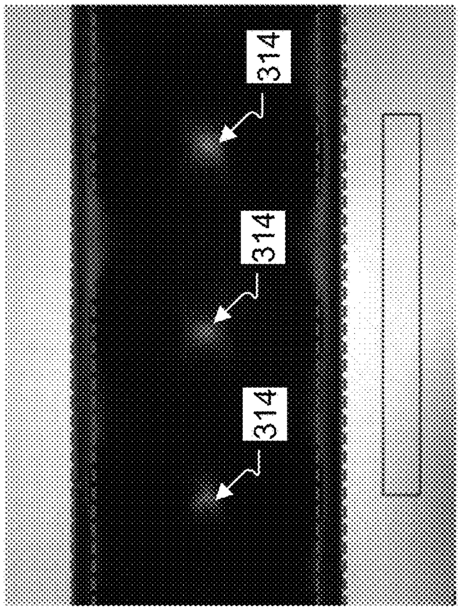
FIG. 3C shows an example of poor plasma separation in an image of a whole blood sample.

In some implementations, the plasma in an image of a whole blood sample may not be well separated from the red blood cells. Such samples may not be suitable for a particular application such as hemolysis detection/measurement. The disclosed technology can be used in such cases to automatically detect and discard such unsuitable samples, e.g., alert a user without further measurement, from further analysis. An example of such a sample image is shown in FIG. 3C, which shows an example of poor plasma separation in an image of a whole blood sample. Specifically, while three plasma ROIs 314 are identified in the image, the small size of the identified ROIs make them prone to inaccurate measurements and hence unsuitable for further analysis. In some implementations, a determination can be made that the size of an ROI (e.g., the ROIs 314) is smaller than a threshold value, and accordingly, the corresponding sample/image can be marked as unsuitable for further analysis and measurements. The threshold value can be a parameter of the microfluidic analysis system that can be configured and modified.

Operations of the process 200 also include performing an analysis of the image of the fluid using the set of pixel values of the ROI (206). In some implementations, performing the analysis of the image of the fluid can include performing measurement of the analyte. In some implementations, the measurement of the analyte can include a parameter indicative of hemolysis (e.g., hemoglobin) in a portion representing blood plasma. For example, the system can be configured to apply an optical density (OD) algorithm or a concentration algorithm to generate a histogram from the pixel values of the ROI, e.g., the ROI corresponding to the plasma region. The system can be further configured to identify the peak of the generated histogram, and use the peak of the histogram to calculate a hemoglobin value. The hemoglobin value can indicate the presence/degree of hemolysis in the blood plasma.

Figure 4A:
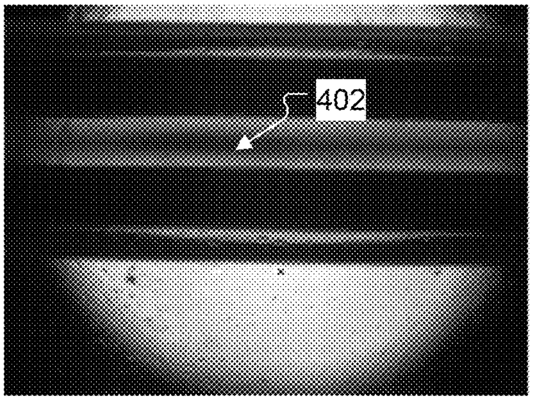
FIG. 4A shows an example of an image of a whole blood sample that includes lipids.

In some cases, identifying an ROI based purely on pixel sample intensity can be challenging, particularly in the presence of sample-dependent source of image variations such as the concentration of light scattering particles such as lipids. The presence of such light scattering particles can make images appear darker than what might be expected in accordance with the light absorbing properties of the particles of interest, and therefore interfere with accuracy of measurements. In some implementations, the operations of the process 200 can further include determining that the ROI excludes a portion that represents lipid in blood plasma, and identifying an updated ROI such that the updated ROI is a bounding box that includes the portion that represents the lipid. FIG. 4A shows an example of an image of a whole blood sample that includes lipids. Lipid particles can cluster near the center of the flow channel when acoustic energy is imparted to the fluidic channel. This type of lipid clustering can result in darker pixels 402 near the center of the flow channel.

Figure 4B:
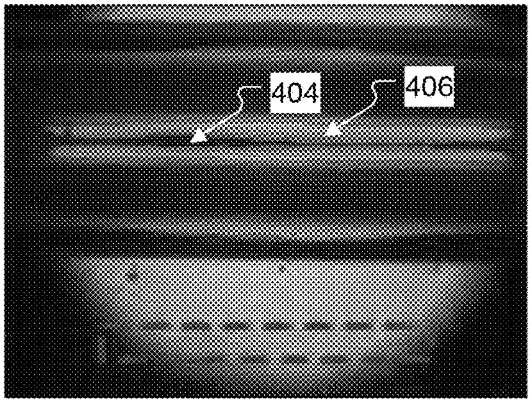
FIG. 4B shows an example of an initial ROI that excludes the lipids.

FIG. 4B shows an example of an initial ROI that excludes the lipids. When a clustering-based thresholding of pixel values is performed within the candidate region to identify the ROI, the dark pixels 404 that correspond to the lipids may be excluded from the ROI because those pixels have pixel values that are below the threshold value identified by the clustering-based thresholding algorithm. The threshold value can be a parameter of the microfluidic analysis system that can be configured (e.g., via programming into a memory such as EEPROM) and modified as needed. Consequently, the measurements performed in the identified ROI 406 may not be accurate. In some implementations, additional processing may be performed based on the identified ROIs such that the lipid pixels are included within the automatically identified ROI. For example, the system can estimate the amount of lipid pixels detected in the initial ROI identified by the clustering-based method. The system can determine whether the estimated amount of lipid exceeds a pre-defined lipid concentration threshold. If the system determines that the estimated amount of the lipid exceeds the pre-defined lipid concentration threshold, a bounding box 408 can be generated around the initial ROI to include the lipid pixels. The bounding box 408 can include both the ROI 406 and the dark pixels 404 that correspond to the lipids. Therefore, the system can generate an updated ROI that corresponds to the region of the bounding box 408 such that the updated ROI includes the lipids.

Figure 5A:
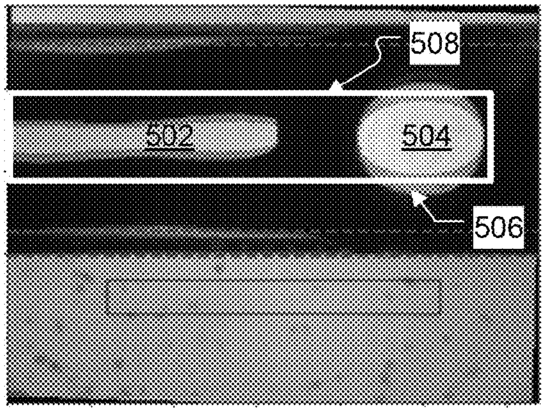
FIG. 5A shows an example of an initial ROI that includes an air bubble.
Figure 5B:
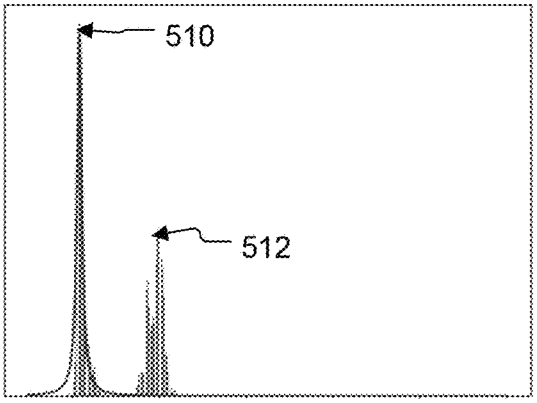
FIG. 5B shows an example of an optical density (OD) histogram of the initial ROI.

In some implementations, the quality determination of the fluid, the fluidic path, or the measuring system can include determining that the ROI includes a portion that represents an air bubble in the fluid, and identifying an updated ROI such that the updated ROI excludes the portion that represents the air bubble because the air bubble may affect the analytical quality of the measurement in the ROI. For example, the pixels for an air bubble are not representative of the hemolysis level in a blood sample, and hence including the air bubble pixels in the measurement can introduce an analytical error. This is shown with examples in FIG. 5A-5E. Specifically, FIG. 5A shows an example of an initial ROI that includes an air bubble. The initial ROI includes a first portion 502 that represents the plasma in the blood sample and a second portion 504 that represents a large air bubble in the blood sample. In this example, the system can calculate an optical density (OD) values for each pixel in the initial ROI, and can plot a histogram of the OD values of the pixels in the initial ROI. The histogram has two peaks 510 and 512, as shown in FIG. 5B. The first peak 510 corresponds to the portion 504 that represents the air bubble in the blood sample, a second peak 512 corresponds to the portion 502 that represents the plasma in the blood sample. Because the air bubble 506 is relatively large, the peak 510 can be higher than the peak 512. Therefore, instead of detecting the peak 512, the system may detect the peak 510 as the highest peak of the histogram, and may calculate an inaccurate hemoglobin value based on the peak 510.

In order to avoid this inaccuracy, a determination may be made that the initial ROI includes an air bubble—by calculating a ROI quality metric of the initial ROI in FIG. 5A. Because plasma ROIs are typically expected to have a particular shape, (e.g., a shape of the flow channel, such as a rectangular shape or a round shape), an index score can be calculated to represent the level of deviation from the expected particular shape. For example, if the plasma ROI is expected to have a rectangular shape, the degree of non-rectangularity can be calculated to determine a likelihood that the initial ROI includes one or more air bubbles.

For example, referring again to FIG. 5A, the system can be configured to generate a bounding box 506 that includes the initial ROI, i.e., the plasma portion 502 and the air bubble portion 504. The area of the initial ROI, i.e., a sum of the plasma portion 502 and the air bubble portion 504, can be calculated, for example, by setting the pixels outside the portions 502 and 504 to zero, and calculating the number of non-zero pixels within the within the bounding box 506. In some implementations, the non-rectangularity may be calculated as:

$$\text{Non-rectangularity} = 1 - (\text{Area of the initial } ROI/\text{Area of the bounding box}). \quad (1)$$

The non-rectangularity is therefore a value between 0 and 1. A smaller non-rectangularity value can indicate that an ROI is more likely to have a rectangular shape. A larger non-rectangularity value can indicate that an ROI is less likely to have a rectangular shape and more likely to have an air bubble. For example, the non-rectangularity value of the initial ROI in FIG. 5A (the portions of 502 and 504) can be 0.7, indicating that the initial ROI is likely to have an air bubble. Other morphological analyses may also be performed to determine whether a particular portion of the determined ROI is likely to be an air bubble (or another gas bubble). For example, a roundness index can be computed for each blob as a ratio of (i) the number of pixels in the blob to (ii) number of pixels in (or an area of) a circle enclosing the blob. In some implementations, if the roundness index for a particular blob is higher than a threshold value (e.g., higher than 0.5), the particular blob is determined as a likely air bubble and may be excluded from being considered as a part of the ROI.

Figure 5C:
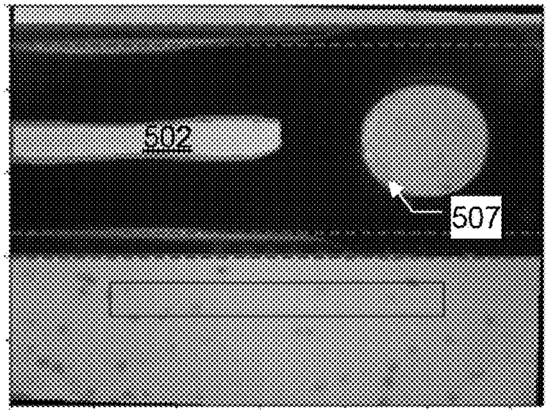
FIG. 5C shows an example of an updated ROI that excludes the air bubble.

In general, once one or more air bubbles are detected, an updated ROI can be generated such that the updated ROI excludes the portion that represents the one or more air bubbles. FIG. 5C shows an example of an updated ROI that excludes the air bubble. In this example, the portion 504 of the initial ROI (FIG. 5A) is determined to correspond to an air bubble 507, and accordingly, an updated ROI only includes the portion 502 that represents the plasma in the blood sample, and excludes the air bubble portion 504.

Figure 5D:
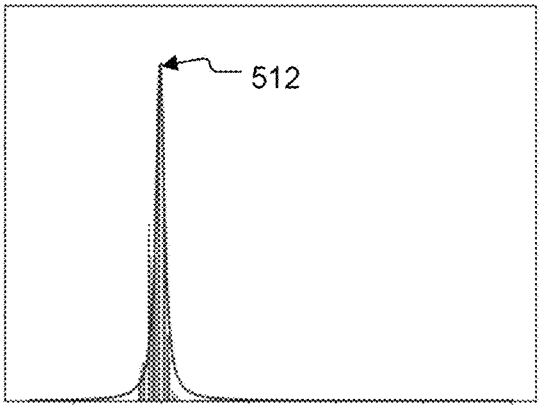
FIG. 5D shows an example of an optical density (OD) histogram of the updated ROI.

The updated ROI can then be used for subsequent processing. For example, when the identified ROI is used for hemolysis detection/measurement, an OD algorithm can be applied to generate a histogram as shown in FIG. 5D. Because the portion 504 corresponding to the air bubble is removed from the updated ROI, the histogram in FIG. 5D only has one peak 512 corresponding to the plasma portion 502. Further calculations based on this are therefore more accurate as compared to that based on the bimodal histogram of FIG. 5B.

Figure 5E:
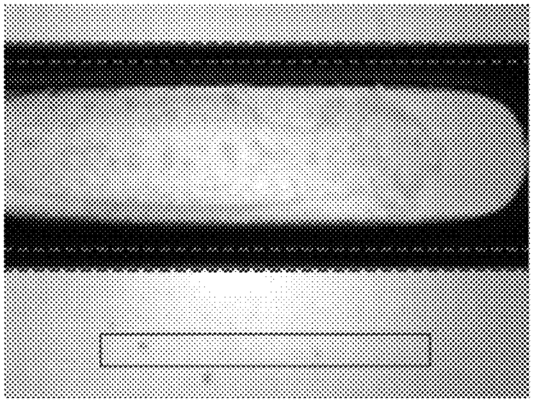
FIG. 5E shows an example of an elongated air bubble in an image of a whole blood sample.

FIG. 5E shows an example of an elongated air bubble in an image of a whole blood sample. In this example, the ROI in the whole blood sample does not have sufficient plasma area. The system can determine that the ROI does not have sufficient plasma area through a set of ROI quality checks. The system can suppress the sample reporting and can alarm an end-user. In some implementations, the set of ROI quality checks can include one or more of the following: 1) abnormal blob height, 2) lack of plasma near flow-cell edges, and 3) elevated blob roundness. Based on the set of ROI quality checks, the elongated bubble pixels can be removed from the ROI and would not be included in a subsequent analysis. In some cases, sufficient plasma pixels can remain in or near another blob(s), and the sample measurement can still be made and reported to the end-user.

In some implementations, correctly identifying an ROI also includes accounting for any unintentional relative tilt between an image capture device (e.g., the camera 104 in FIG. 1) and the container within which the fluid to be imaged is disposed (e.g., the container 102 in FIG. 1). Such tilts or orientation variations can be introduced, for example, during inserting/assembling the fluid container within the test apparatus. For example, when the container is a disposable cartridge, orientation variations or tilts can occur when one cartridge is replaced with another. In some implementations, the technology described herein facilitates detecting an amount of tilt in the image of the fluid, generating, based on the amount of the tilt, a rotation-corrected image of the fluid, and identifying the ROI in the rotation-corrected image.

Figure 6A:
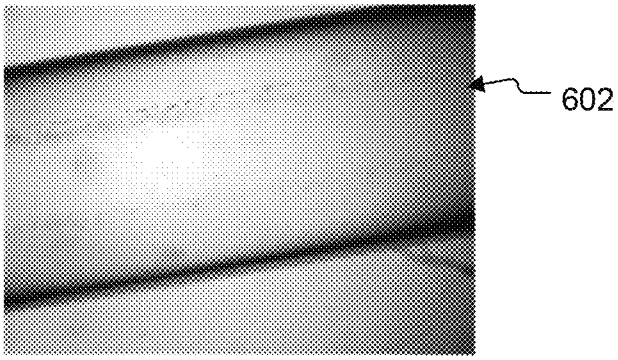
FIG. 6A shows an example of an image of a flow-cell that is tilted.
Figure 6B:
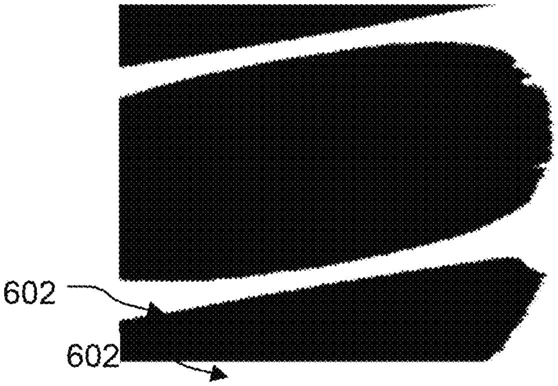
FIG. 6B shows a thresholded image of FIG. 6A.
Figure 6C:
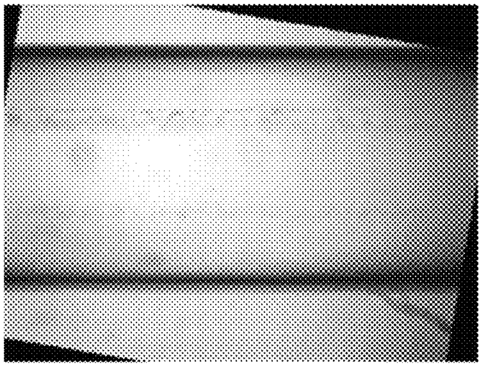
FIG. 6C shows a rotation-corrected image of FIG. 6A.

FIG. 6A shows an example of an image of a fluid that is tilted. The image 602 is a raw image captured by the camera. The image 602 shows misalignment between a camera and a flow-cell. In some implementations, an amount of tilt in the image 602 can be estimated by generating a thresholded image, e.g., by Otsu thresholding, and rotation-correcting the thresholded image. Other implementations may include using an Artificial Neural Network (NN) or a Hough Transform to detect the flow-cell edges and to estimate the tilt angle. FIG. 6B shows a thresholded image generated from the example of FIG. 6A using Otsu thresholding. The tilt angle can be estimated, for example, by calculating an angle of one of the detected edges, e.g., the bottom outer edge 604, with respect to the horizontal boundary of the image. Based on the estimated amount of tilt, a rotation-corrected image of the fluid can be generated. FIG. 6C shows a rotation-corrected image of FIG. 6A. The ROI identification can then be performed on the rotation-corrected image.

Figure 7:
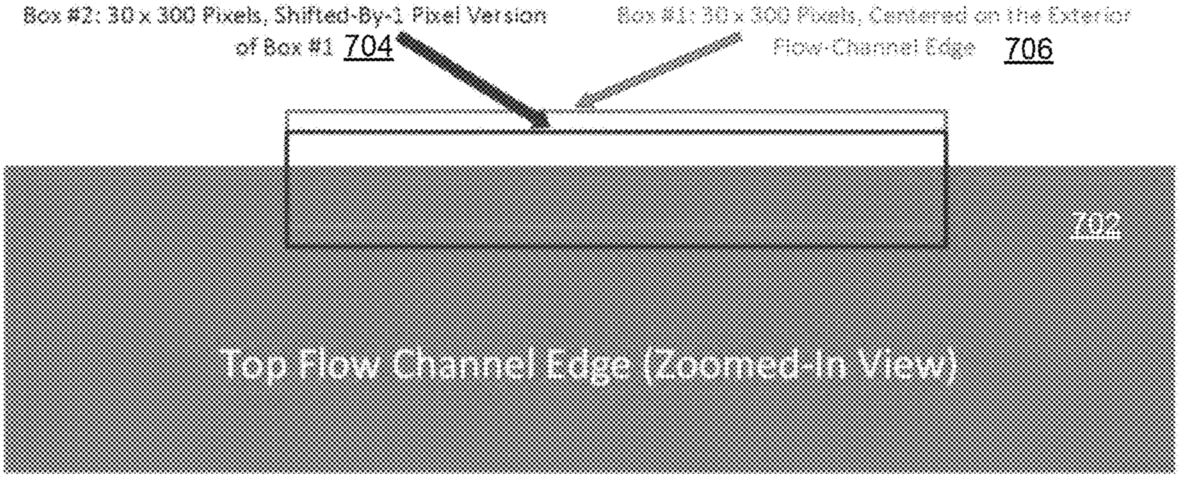
FIG. 7 is a schematic diagram of an example process for generating an image focus score.

In some implementations, performing sample quality evaluation can include generating an image focus score associated with the image, determining that the image focus score is lower than a predetermined threshold, and discarding the image of the fluid in response to determining that the image focus score is lower than the predetermined threshold. Intrinsic and fixed image features such as sharp edges can be used as a target for image focus evaluation, providing an advantage over the traditional approach where an external target is introduced to evaluate the image focus. FIG. 7 shows an example of generating an image focus score by measuring contrasts of pixels near an edge in the image. FIG. 7 includes a region 702 that corresponds to a zoomed in view of the top outer edge of the flow-cell. The box #1 (706) has 30×300 pixels, and is centered on the exterior flow-channel edge. The box #2 (704) has 30×300 pixels, and is a box that is generated by shifting the box 706 by one pixel downward. In some implementations, an image focus score can be generated by performing the following steps: (1) normalizing every pixel by an overall image brightness; (2) summing the normalized pixels across the columns in Box 706, wherein the result will be a first 30×1 array of values; (3) summing the normalized the pixels across the columns in Box 704, wherein the result will be a second 30×1 array of values; (4) estimating a two point derivative by subtracting the second array from the first array; (5) determining the maximum absolute value of the two point derivative, wherein the maximum absolute value is an estimated focus score of the top outer edge; (6) repeating steps (2)-(5) for the bottom outer edge of the flow-cell; and (7) generating an average focus score based on the estimated focus scores for the top outer edge and the bottom outer edge. Other types of image focus estimation metrics, such as a Brenner function score, may also be used. In some implementations images with focus scores less than a threshold may be discarded, for example, because measurements performed on an out-of-focus image may be compromised. In some implementations, the system can generate an alert in response to discarding an image.

In some implementations, determining sample-specific ROIs can include accounting for variations due to illumination from one sample to another. For example, power fluctuations in the light source (e.g., an LED) can introduce variations in the brightness of corresponding images captured by the camera. Specifically, when the camera captures two images at two different times, the images may show different brightness due to the fluctuation of the LED power. In some implementations, performing the analysis of the image of the fluid can include identifying, in the image, a reference portion (e.g., a transparent, e.g., glass, portion of the container), and using brightness of the reference portion to normalize/evaluate brightness of other portions of the image.

Figure 8A:
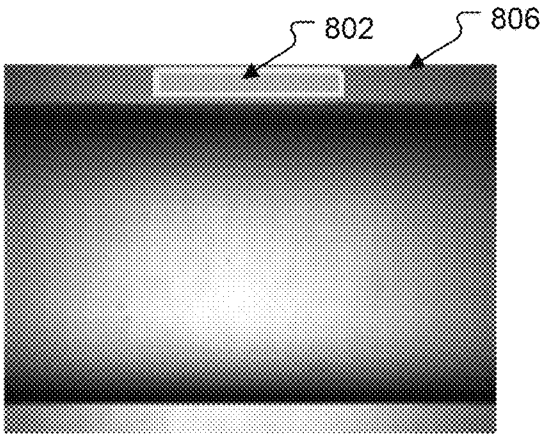
FIG. 8A shows an example of a portion of a reference image, the portion representing a transparent region.
Figure 8B:
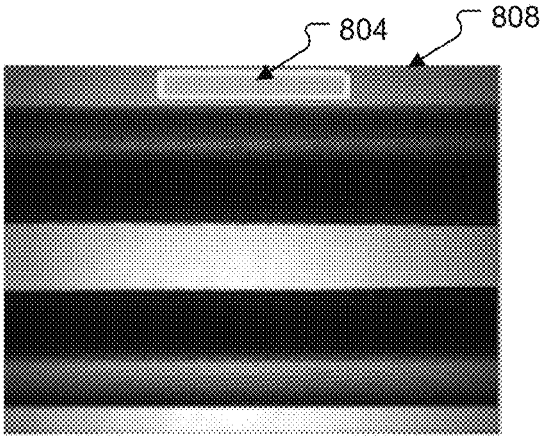
FIG. 8B shows an example of a portion of an image of a whole blood sample, the portion representing a transparent region.

For example, when executing an OD algorithm, both a reference image without a blood sample and an image with a blood sample can be captured and compared with one another. Referring to the example in FIG. 8A, the system can identify, in the reference image 806, a portion representing a transparent, e.g., glass, portion 802 of the container. The system can also identify, in the blood sample image 808 (FIG. 8B), a corresponding portion 804 representing a transparent portion of the container. The brightness of the transparent portion can be used as a reference point to evaluate the brightness of other portions of the image. For example, the system can compensate for the brightness variation between the reference image 806 and the blood sample image 808 by comparing the brightness of the corresponding transparent portions 802 and 804. In executing an OD algorithm, an optical density can be generated, for example, by normalizing the pixel value in the reference image and blood sample image with the pixel value in their respective transparent portions. For example, the OD calculation can be the following:

$$OD = \log\left(\frac{Ref/I_0}{\text{Sample}/I_1}\right). \tag{2}$$

Here, Ref is a pixel value in the reference image 806. Blood is a pixel value of a corresponding pixel in the blood sample image 808. $I_0$ is the brightness of the transparent region 802 in the reference image 806, and $I_1$ is the brightness of the transparent region 804 of the blood sample image 808.

In some implementations, one or more optical characteristics of the on-board calibration solutions may be monitored at predetermined intervals to ensure continued quality checks, and to potentially calibrate analytical performance. For example, the system can monitor for residual blood clots, lipids, air bubbles, image focus, and so on, at predetermined intervals. In some implementations, this can include identifying a target optical interference pattern in the image, and generating an alert in response to identifying the target optical interference pattern. Examples of the target optical interference patterns can include interference patterns representing air bubbles, debris in the field-of-view, and carryover material from the sample, etc.

Referring back to FIG. 3C, the image shows an example of poor plasma separation in a whole blood sample detected through a quality monitoring process described above. Similarly, FIG. 5E shows an example of an elongated air bubble in an image of a whole blood sample. Upon detecting such poor plasma separation, elongated air bubble, or other artifacts that potentially compromises the accuracy of the results, the system can be configured to generate an alert and/or exclude the image from further processing. After receiving the alert, a user may manually review the image, or decide to discard the image.

In some implementations, other tests can be performed on the identified ROI in the fluid sample, e.g., colorimetric measurements of analytes in blood. The system can determine the ROI in a similar way as the system determines an ROI for a hemolysis test. In some implementations, the system can determine the ROI based on the specific test that is to be performed. For example, the system can determine the ROI based on areas of the image that changes color in response to one or more of the following: an analyte present in the sample, antibody/antigen binding reaction, and staining targeting specific parts of the cell.

The system can be configured to allow a user to choose or automatically choose a particular test among different tests such that parameters for a particular test (e.g., preprogrammed parameters) can be determined based on the chosen test. In some implementations, the system can allow a user to enter desired parameters for a test (e.g., desired sensitivity and/or specificity levels in performing an analysis).

Figure 9:
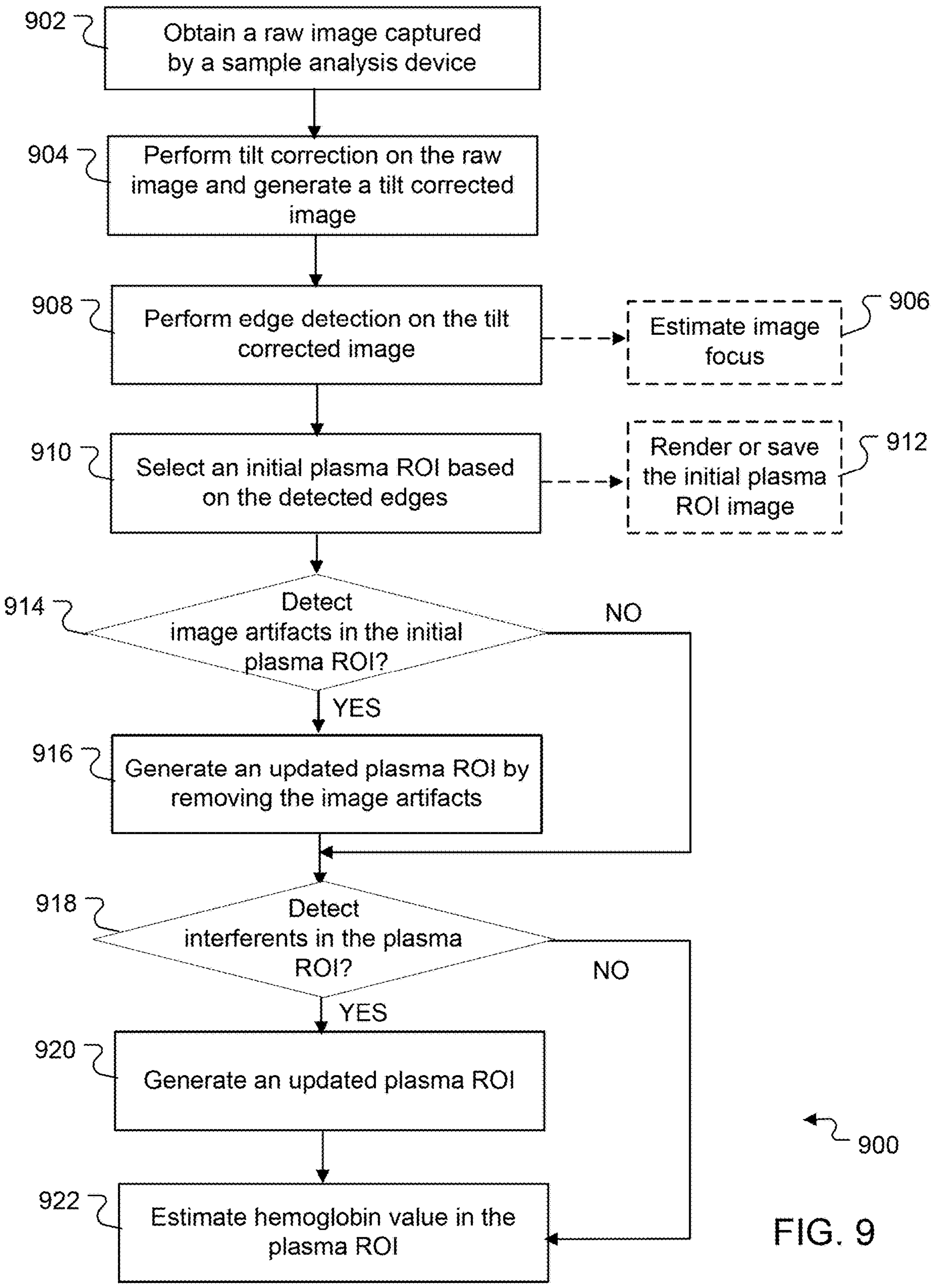
FIG. 9 is a flowchart of an example process for performing blood sample analysis in accordance with technology described herein.

FIG. 9 is a flowchart of an example process 900 for performing blood sample analysis in accordance with technology described herein. The example process 900 includes an example imaging process (e.g., steps 902, 904, 906, 908, 910, and 912). The example process 900 also includes an example quality monitoring process (e.g., steps 904, 906, 914, 916, 918, 920). In some implementations, at least a portion of the process 900 may be executed by one or more processing devices associated with the microfluidic analysis system 112 described with reference to FIG. 1. In some implementations, at least a portion of the process 900 may be executed by the optical module 101. In some implementations, at least a portion of the process 900 may be executed at one or more servers (such as servers or computing devices in a distributed computing system) in communication with the sample analysis device 100 described with reference to FIG. 1.

Operations of the process 900 include obtaining a raw image captured by a sample analysis device (902). The raw image can be an image of a whole blood sample with blood plasma separated from red blood cells. For example, the optical module 101 in FIG. 1 can capture the raw image. In some implementations, the system can obtain multiple groups of images as input to the process 900. The multiple groups of images can include one or more frames of dark images, one or more frames of reference images, and one or more frames of sample images. Dark images are captured to account for optical dark signal from the electronics. Reference images are captured to compensate for light transmission without the sample fluid. Each image frame can include one or more color images (e.g., a red image and a yellow image). In some implementations, the system can generate an image that is ready for subsequent analysis from the multiple groups of images. The system can perform image subtraction to compensate for contributions from electronic and optical noise. For example, the system can subtract the dark images from the sample images. As another example, the system can subtract the dark yellow image from the sample yellow image. In some implementations, the system can smooth the raw image (or an image resulting from the subtraction process) by applying a smoothing filter such as a Gaussian blur filter.

Operations of the process 900 also include performing tilt correction on the raw image and generating a tilt corrected image (904). For example, the system can perform the tilt correction in accordance with the techniques described in connection with FIGS. 6A-6C. In some implementations, the system can import a single frame (e.g., the first frame) of a sequence of images and perform the tilt correction based on the single frame of the sequence of images. For example, the system can import the first frame of the blood sample images (e.g., including the red image and the yellow image), and can estimate the flow cell tilt angle with the red image of the first frame of the blood sample image. The system can then perform the tilt correction on the one or more frames of sample images and one or more frames of blood sample images using the flow cell tilt angle estimated with the red image of the first frame of the blood sample images.

In some implementations, the operations of the process 900 can optionally include estimating an image focus of the tilt corrected image (906). For example, the system can estimate an image focus score in accordance with the techniques described in connection with FIG. 7. For example, the system can estimate an image focus score on a yellow blood sample image. The system can determine whether the image focus score is lower than a predetermined threshold, and if so, discard the image and obtain another image.

Operations of the process 900 also include performing edge detection on the tilt corrected image (908). Operations of the process 900 also include selecting an initial plasma ROI based on the detected edges (910). For example, the system can perform the edge detection and ROI selection in accordance with the techniques described in connection with FIGS. 3A-3B. Similar to the tilt correction in step 904, in some implementations, the system can import a single frame (e.g., the first frame) of a sequence of images and perform the edge detection based on the single frame of the sequence of images. For example, the system can import the first frame of the blood sample images (e.g., including the red image and the yellow image), and can detect the flow cell edges using the yellow image of the first frame of the blood sample image. Then the system can determine the initial plasma ROI based on the detected flow cell edges.

In some implementations, the operations of the process 900 can optionally include rendering the initial plasma ROI on a display or saving the initial plasma ROI as an image (912). For example, the system can render the initial plasma ROI on a display such that a user can review the ROI, determine the quality of the ROI, or perform analysis of an analyte in the ROI. As another example, the system can save the initial plasma ROI as an image (or a video if the input to the system is multiple frames of images) in the memory or hard drive of a local computer or a remote server, such that the image can be retrieved and analyzed (either manually or using a software) at a later time.

Operations of the process 900 can also include detecting image artifacts (e.g., an air bubble) in the initial plasma ROI (914). If the system determines that an image artifact is in the initial plasma ROI, the operations of the process 900 can include generating an updated plasma ROI by removing the image artifact (916). If the system determines that the initial plasma ROI does not include an image artifact, the system can execute step 918 directly. For example, the system can perform the air bubble detection and removal in accordance with the techniques described in connection with FIGS. 5A-5D. In some implementations, the system can calculate a non-rectangularity and/or perform blob analysis. Because the plasma ROI typically has a rectangular shape, a wavy appearance or a blob shape can indicate the presence of air bubbles or other fluidic and plasma separation issues. In some implementations, the system can first generate an OD image (e.g., a red OD image and/or a yellow OD image) and can calculate % CV (i.e., the coefficient of variation) within the OD image (e.g., % CV within the yellow plasma OD image). The system can detect one or more air bubbles using a predetermined rule. For example, if (i) the non-rectangularity is larger than 0.45, (ii) the number of blobs is larger than one, and (iii) the % CV in the yellow OD is larger than 45, the system can determine the image has at least one air bubble. If a suspected air bubble is detected, the system can redraw the plasma ROI by excluding the suspected air bubble (e.g., one or more round blobs). In some implementations, if the system has already estimated a hemoglobin value in the initial plasma ROI, the system can repeat the hemoglobin value estimate process for the updated ROI and generate an updated hemoglobin value.

Figure 4C:
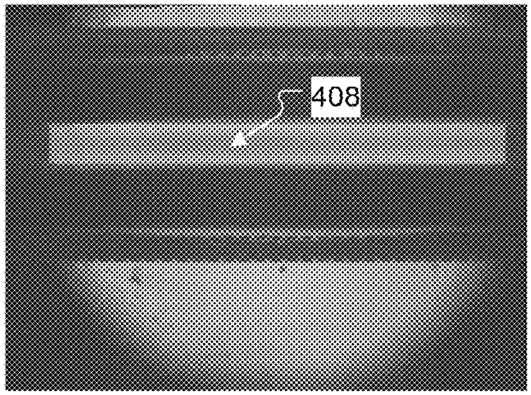
FIG. 4C shows an example of an updated ROI that includes the lipids.

Operations of the process 900 can also include detecting interferents (e.g., high lipid, clots) in the plasma ROI (918). If the system determines that interferents are in the plasma ROI (e.g., the initial ROI, or the updated ROI after removing the air bubble), the operations of the process 900 can include generating an updated plasma ROI (e.g., by including or removing the interferences) (920). If the system determines that the plasma ROI does not include interferents, the system can go directed to step 922 of the process 900. For example, the system can perform the high lipid detection in accordance with the techniques described in connection with FIGS. 4A-4C. After determining high lipid exists in the initial plasma ROI, the system can include the high lipid by redrawing the plasma ROI. For example, the system can first use a bounding box to include the initial ROI and the system can reduce the height of the bounding box to a predetermined percentage of the original height (e.g., 75% of the original height). The region of the bounding box at the reduced height is the updated plasma ROI that includes the high lipids. In some implementations, if the system has already estimated a hemoglobin value in the initial plasma ROI or the updated plasma ROI after removing one or more air bubbles, the system can repeat the hemoglobin value estimate process for the updated plasma ROI that includes the high lipid and generate an updated hemoglobin value.

Operations of the process 900 can also include estimating hemoglobin value in the plasma ROI (922). The system can estimate the hemoglobin value using an OD algorithm or a concentration algorithm. For example, with the OD algorithm, the system can calculate a red plasma OD image and a yellow plasma OD image. The system can calculate a peak value in the yellow OD image and a peak value in the red OD image by histogram fitting. The system can apply the extinction coefficients to the peak value to estimate the hemoglobin value. For example, with the concentration algorithm, the system can calculate a red plasma OD image and a yellow plasma OD image. The system can estimate the hemoglobin value using the concentration algorithm. For example, in the concentration algorithm, extinction coefficients can be applied before the histogram fitting step.

In some implementations, the operations of the process 900 can also include a glass correction (i.e., intensity normalization) process. When calculating the OD images, e.g., with the OD algorithm or the concentration algorithm, the system can perform a glass correction process in accordance with the techniques described in connection with FIGS. 8A-8B. For example, the system can select the glass area (i.e., the glass ROI) in a red blood sample image based on the location of the flow cell edges detected in step 908. The system can calculate the average intensity in the glass ROI for both the reference image and the blood sample image. The system can also calculate the average intensity in the plasma ROI for the reference image and the sample image. The system can perform the glass correction based on the average intensities in the glass ROI and the plasma ROI, e.g., following equation (2).

Various implementations of the systems and techniques described here can be realized in digital electronic circuitry, integrated circuitry, specially designed application specific integrated circuits (ASICs), computer hardware, firmware, software, and/or combinations thereof. These various implementations can include implementation in one or more computer programs that are executable and/or interpretable on a programmable system including at least one programmable processor, which may be for a special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural, object-oriented, assembly, and/or machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a cathode ray tube (CRT) or liquid crystal display (LCD) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a GUI or a web browser through which a user can interact with an implementation of the systems and techniques described here), or any combination of such back end, middleware, or front end components. The components of the system can be interconnected by any form or medium of digital data communication, such as network 210 of FIG. 2. Examples of communication networks include a LAN, a WAN, and the Internet.

The computing system can include clients and servers. A client and server are generally remote from each other and typically interact through a communication network. The relationship of client and server arises by virtue of computer programs running on the respective computers and having a client-server relationship to each other.

Although a few implementations have been described in detail above, other modifications may be made without departing from the scope of the inventive concepts described herein, and, accordingly, other implementations are within the scope of the following claims.

What is claimed is:

1. A computer-implemented method comprising:

obtaining pixel values corresponding to a container of a microfluidic analysis system, wherein the microfluidic analysis system comprises or receives the container and the container contains a fluid for measurement of analyte or quality determination of a fluid, fluidic path, or measuring system;

identifying a region of interest (ROI), wherein the ROI corresponds to a first set of the pixel values; and using the first set of pixel values in the measurement of the analyte or the quality determination.

2. The method of claim 1, wherein identifying the ROI corresponding to the first set of the pixel values comprises identifying, based on at least a plurality of the pixel values, a particle free region of the fluid.

3. The method of claim 1, further comprising identifying, using the pixel values, a transparent portion of the container corresponding to a second set of the pixel values and using brightness of the second set of the pixel values as a reference point to evaluate brightness of others of the pixel values.

4. The method of claim 1, wherein obtaining comprises receiving the pixel values from an optical sensor of the microfluidic analysis system.

5. The method of claim 1, wherein identifying the ROI corresponding to the first set of pixel values comprises:

detecting a plurality of reference features associated with the container of the fluid;

identifying, based on the reference features, a candidate region for the ROI; and performing clustering-based thresholding of pixel values within the candidate region to identify a portion representing blood plasma or using one or more neural networks for identifying the ROI.

6. The method of claim 1, wherein the measurement of the analyte comprises a parameter indicative of hemolysis (hemoglobin), lipemia (or lipids), Icterus (or bilirubin), or a combination thereof, in a portion representing blood plasma.

7. The method of claim 1, further comprising:

determining that the ROI excludes a portion that represents lipid in blood plasma; and identifying an updated ROI such that the updated ROI comprises a bounding box that includes the portion that represents the lipid.

8. The method of claim 1, wherein the quality determination of the fluid, the fluidic path, or the measuring system comprises: determining quality of an assay, determining quality of a sample, and determining integrity of the fluidic path or the measuring system impacting the ROI.

9. The method of claim 1, wherein the quality determination of the fluid, the fluidic path, or the measuring system comprises:

determining that the ROI includes a portion that represents an air bubble in the fluid; and identifying an updated ROI such that the updated ROI excludes the portion that represents the air bubble.

10. A system comprising:

a microfluidic analysis apparatus that comprises or receives a container configured to hold a fluid for measurement of analyte or quality determination; an optical sensor configured to obtain pixel values for the fluid in the container; and one or more processing devices configured to:

identify, based on the pixel values, a region of interest (ROI), wherein the ROI corresponds to a first set of the pixel values, for use in the measurement of the analyte or the quality determination of the fluid, fluidic path, or the microfluidic analysis apparatus.

11. The system of claim 10, wherein the one or more processing devices is configured to identify, using the pixel values, a transparent portion of the container corresponding to a second set of the pixel values and to use brightness of the second set of the pixel values as a reference point to evaluate brightness of others of the pixel values.

12. The system of claim 10, wherein identifying the ROI corresponding to the first set of the pixel values comprises identifying, based on at least a plurality of the pixel values, a particle free region of the fluid.

13. The system of claim 10, wherein the optical sensor is configured to obtain the pixel values by receiving the pixel values from an optical sensor of the microfluidic analysis system.

14. The system of claim 10, wherein identifying the ROI comprises identifying, in an image, a portion representing blood plasma, wherein identifying the portion representing the blood plasma comprises:

detecting a plurality of reference features associated with the container of the fluid;

identifying, based on the reference features, a candidate region for the ROI; and performing clustering-based thresholding of pixel values within the candidate region to identify the portion representing the blood plasma or using one or more neural networks for identifying the ROI.

15. The system of claim 10, wherein the measurement of the analyte comprises a parameter indicative of hemolysis (hemoglobin), lipemia (or lipids), Icterus (or bilirubin), or a combination thereof, in a portion representing blood plasma.

16. The system of claim 10, wherein the one or more processing devices is configured to:

determine that the ROI excludes a portion that represents lipid in blood plasma; and identify an updated ROI such that the updated ROI comprises a bounding box that includes the portion that represents the lipid.

17. The system of claim 10, wherein the quality determination of the fluid, the fluidic path, or the measuring system comprises: determining quality of an assay, determining quality of a sample, and determining integrity of the fluidic path or the measuring system impacting the ROI.

18. The system of claim 10, wherein the quality determination of the fluid, the fluidic path, or the measuring system comprises:

determining that the ROI includes a portion that represents an air bubble in the fluid; and identifying an updated ROI such that the updated ROI excludes the portion that represents the air bubble.

19. A non-transitory, computer-readable medium storing one or more instructions executable by a computer system to perform operations comprising:

obtaining pixel values corresponding to a fluid of a microfluidic analysis system, wherein the microfluidic analysis system comprises or receives a container that contains the fluid for measurement of analyte or quality determination, and the pixel values are captured using an imaging device associated with the microfluidic analysis system;

identifying, based on the an image, a region of interest (ROI), wherein the ROI is a set of pixel values for use in the measurement of analyte or the quality determination of the fluid, fluidic path, or measuring system;

wherein identifying the ROI is based on information about the measurement of the fluid or based on information about non-analyte features of the fluid; and performing an analysis of the image of the fluid using the set of pixel values of the ROI.

20. The non-transitory, computer-readable medium of claim 19, wherein identifying the ROI comprises identifying, in the image, a portion representing blood plasma, wherein identifying the portion representing the blood plasma comprises:

detecting a plurality of reference features associated with the container of the fluid;

identifying, based on the reference features, a candidate region for the ROI; and performing clustering-based thresholding of pixel values within the candidate region to identify the portion representing the blood plasma.

* * * * *